US005767107A

United States Patent [19]
Chaundy et al.

[11] Patent Number: 5,767,107
[45] Date of Patent: Jun. 16, 1998

[54] COMPOSITIONS CONTAINING GLUTEN AND POLYSACCHARIDES THAT CONTAIN URONIC ACID RESIDUES USEFUL FOR ENCAPSULATING FATS, OILS AND SOLIDS

[75] Inventors: Frederick K. Chaundy, Grosse Ile; Scott P. Melidosian, Allen Park; Rudolph E. Lisa, Grosse Ile; Jeffrey L. Finnan, Dearborn, all of Mich.

[73] Assignee: BASF Corporation, Mount Olive, N.J.

[21] Appl. No.: 697,939

[22] Filed: Sep. 3, 1996

[51] Int. Cl.$^6$ ............... C08B 37/04; C08B 37/06; C07H 13/02; C07H 1/00
[52] U.S. Cl. ............... 514/54; 536/2; 536/3; 536/119; 536/123.1
[58] Field of Search ............... 536/2, 3, 119, 536/123.1; 514/54

[56] References Cited

U.S. PATENT DOCUMENTS

| | | | |
|---|---|---|---|
| 3,351,531 | 11/1967 | Beatrice Foods | 426/98 |
| 3,786,123 | 1/1974 | Hanssi | 264/53 |
| 3,952,109 | 4/1976 | Rao et al. | 426/48 |
| 4,911,942 | 3/1990 | Yajima | 426/455 |
| 4,935,257 | 6/1990 | Yajima | 426/555 |
| 5,074,902 | 12/1991 | Connick et al. | 504/117 |
| 5,358,863 | 10/1994 | Quimby et al. | 435/178 |
| 5,418,010 | 5/1995 | Janda et al. | 427/213.31 |
| 5,512,268 | 4/1996 | Grinstaff et al. | 424/9.322 |

FOREIGN PATENT DOCUMENTS 918168  2/1963  United Kingdom.

*Primary Examiner*—John Kight
*Assistant Examiner*—Everett White
*Attorney, Agent, or Firm*—Joanne P. Will

[57] ABSTRACT

The present invention relates to compositions useful for encapsulating fats, oils or solids, comprising gluten and polysaccharides that contains uronic acid residues.

12 Claims, No Drawings

COMPOSITIONS CONTAINING GLUTEN AND POLYSACCHARIDES THAT CONTAIN URONIC ACID RESIDUES USEFUL FOR ENCAPSULATING FATS, OILS AND SOLIDS

FIELD OF THE INVENTION

The present invention relates to biodegradable compositions containing gluten and polysaccharides that contain uronic acid residues useful for encapsulating fats, oils and solids. Said compositions are useful for administering various ingredients in fat, oil and solid forms, such as fragrances, flavors, vitamins, agricultural chemicals, and pharmaceutical agents.

BACKGROUND OF THE INVENTION

Gluten is the protein fraction of the wheat or corn kernel. Specifically, vital wheat gluten is the water-insoluble complex protein fraction separated from wheat or wheat flour. In its freshly extracted wet form it is known as gum gluten which when dried yields a cream-to-tan, free flowing powder of high protein content and bland taste. When re-hydrated, it regains its original characteristics. So unique is the functionality of wheat gluten and so persistent is the structural integrity after cooking, it is commercially important and it appears to have no functional competitor. Corn gluten or zein has similar chemistry and is also commercially important despite its higher cost.

However, the water insolubility of gluten can limit its usefulness. Commonly, those skilled in the art solubilize gluten using acids or bases. Corn gluten is soluble in some organic solvents, such as alcohols. However, solvent recovery is an issue which adds to the cost of the process. In many such applications, the addition of an acid or base is inconvenient, since they would end up in the solid product, and could resolubilize the gluten, a potentially undesirable result. If an organic acid is used to solubilize gluten, it may be flashed off during drying. This can result in recovery problems to prevent pollution (infact, gluten is dried in just this way). An additional potential method, the use of enzymes to reduce the molecular weight of the gluten and thereby increase the solubility would have other drawbacks, lowering the molecular weight, which would probably destroy part of the film forming capability of the gluten, making its use less desirable as a protective encapsulator.

Once solubilized, gluten can be used in a wide range of applications. It can be used in film forming (i.e. binding or adhesive properties), it has thermosetting properties, large water absorption capabilities, has bland or slight cereal flavor properties, as well as visco-elastic properties. It's water absorptive properties are used to extend shelf-life of many foods. It is used as a binding and adhesive agent in meats, and is capable of forming glazing meat surfaces. It is used by the baker to adjust flour protein level, and is used for its visco-elastic properties to improve bakery dough strength. It is used to fortify cereal with extra protein, and helps to bind vitamin-minerals in enriched breakfast cereal formulas. Wheat gluten imparts texture and eating quality to synthetic cheeses, and replaces more expensive sodium caseinate in several imitation cheese products. Gluten is also often used in extruded snack foods, tortillas, Japanese surimi, breading, batter mixes, coatings, and flavoring. It is used in canned pet food for binding and moisture absorbing properties. It is used in aquaculture for adhesive properties in granule forms of fish food. Its use is wide and pervasive, in part because it has GRAS status (generally recognized as safe) by the U.S. Food and Drug Administration. Zein or corn gluten has similar properties except it is not viscoelastic and, therefore, not useful in improving bakery dough strength.

Other useful applications for gluten include: encapsulating weed and pest control agents, flavorings, vitamins, medicaments, imaging agents for MRI (Magnetic resonance imaging) usage, preparing fragrance, flavoring and vitamin compositions, and sprayable formulations for pest control.

Specifically, EP 0 357 169 B discloses a process for preparing a vitamin powder wherein the vitamin is added to acid- or base-solubilized gluten and then spray dried to form the powder. GB 918,168 discloses a powdered feed supplement composition wherein vitamin bearing oils are encased within a protective protein shell such as soy flour or gluten. Said feed supplement is prepared by spray drying. Said soy flour or gluten is solvent extracted. U.S. Pat. Nos. 3,786,123 and 5,418,010, disclose a microencapsulation process wherein the core material (vitamins, minerals, and flavorings in liquid or solid form) is encapsulated with an animal or vegetable protein, such as an acid- or base-solubilized gluten; and the encapsulation takes place via an extruder. U.S. Pat. No. 4,911,942 discloses stabilized oil and fat powders wherein said oil or fat is coated with an acid- or base-solubilized gluten. The powder is formed by spray drying or vacuum drying. U.S. Pat. No. 5,512,268 discloses imaging agents for NMRI (nuclear magnetic resonance imaging) encapsulated in gluten which are injectable into the human body. U.S. Pat. Nos. 5,358,863; 5,074,902, and 5,358,863 all disclose weed and pest control agents encapsulated in gluten. Finally, U.S. Pat. No. 3,351,531 discloses gluten as an encapsulating agent for oil-in-water dispersions. The gluten is solubilized with acetic acid or ammonia before it can be used to encapsulate the oil in water emulsion.

Applicants have now discovered novel gluten compositions containing polysaccharides that contain uronic acid residues useful for encapsulating oils or solids. The polysaccharides that contain uronic acid residues solubilize the gluten without the need for acids and bases as required by the art. The elimination of the acid or base solubilization allows working at a neutral pH. The process for solubilizing the gluten with polysaccharides that contain uronic acid residues is disclosed in U.S. Pat. No. 5,738,805 entitled: "Process for Solubilizing Gluten That Normally Is Capable of Absorbing Water Without Dissolution", which describes a method of solubilizing gluten without the use of acids or bases. It uses a polysaccharide that contains uronic acid residues to dissolve the gluten. When gluten is solubilized with a polysaccharide that contains uronic acid residues said gluten is a cost effective substitute for applications requiring gelatin, since gluten is much cheaper than gelatin.

Specifically, this application relates to compositions comprising fats, oils or solids encapsulated in a composition comprising gluten and polysaccharides that contain uronic acid residues, wherein a neutral pH is maintained. Since many compounds, such as vitamins, are affected by extremes of pH, a neutral pH is of great utility. Further, acid or base recovery is not an issue and processing costs are reduced.

DEFINITIONS AND USAGES OF TERMS

The term "beadlet", as used herein, refers to substantially spherical particles which are primarily between about 105 microns and about 840 microns in diameter.

The term "free-flowing ", as used herein, refers to powders or beadlets having a FLODEX flowability of 50 or more. The FLODEX flowability test is described in detail in U.S. Pat. No. 5,000,888, column 7, lines 55–70, column 8, lines 1–45, incorporated by reference herein.

SUMMARY

A composition useful for encapsulating fats, oils and solids comprising:
(a) 14.5 to 97% gluten;
(b) a polysaccharide that contains uronic acid residues, wherein said polysaccharide that contains uronic acid residues is at least 3% of the level of the gluten
(c) 0.0 to 95% water Further, the compositions of the present invention can be free-flowing powders, free-flowing beadlets or liquids. The free-flowing powders and beadlets are obtained by spray drying, modified spray drying, spray formulation, double emulsion, and salt precipitation in an inert carrier to remove water. Conversely, the water need not be removed if a liquid composition is desired.

All percentages are on a weight percent basis unless otherwise indicated.

DETAILED DESCRIPTION

A composition useful for encapsulating fats, oils and solids comprising:
(a) 14.5 to 97% gluten;
(b) a polysaccharide that contains uronic acid residues, wherein said polysaccharide that contains uronic acid residues is at least 3% of the level of the gluten
(c) 0.0 to 95% water Further, the compositions of the present invention can be free-flowing powders, free-flowing beadlets or liquids. The free-flowing powders and beadlets are obtained by spray drying, modified spray drying, spray congealing, spray formulation, double emulsion technique, or salt precipitation in an inert carrier to remove water, or the water is not removed if a liquid composition is desired.

Fats and Oils Useful in the Practice of the Present Invention

Fats and oils useful in the practice of the present invention include, but are not limited to, flavoring and fragrance oils, vegetable oils, animal fats, and natural and synthetic vitamins such as A,D,E and K. Preferably, the oils are vitamin oils. Vitamin oils are preferred. The most preferred vitamin oils are A and D. Preferably, fats and oils are used at levels of 0.01 to 85%, more preferably 0.01 to 70%, most preferably 0.01 to 40% by weight.

Solids Useful in the Practice of the Present Invention

Solids useful in the practice of the present invention include, but are not limited to, pesticides, herbicides, fungicides, growth regulators, fertilizers, and solid forms of natural and synthetic vitamins, such as the C and B vitamins, said B vitamins including, but not limited to folic acid, riboflavin, pyridoxine, niacin, and thiamine. Other useful solids are animal fats and pharmaceuticals. Representative solid pharmaceuticals include, but are not limited to antiinfectives such as antibiotics, and antiviral agents, analgesics, anorexics, antihelminthics, anti arthritics, antiasthmatics, anticonvulsants, antidepressants, antidiabetic agents, antidiarrheals, antihistamines, antiinflammatory agents, antimigraine preparations, anti nauseants, antineoplastics, antiparkinsonism drugs, antipruritics, antipsychotics, antipyretics, antispasmodics, anticholinergics, sympathomimetics, xanthine derivatives, cardiovascular preparations including calcium channel blockers, and beta blockers, and anti arrythmics, antihypertensives, diuretics, vasodilators including general coronary, peripheral and cerebral, central nervous system stimulants, cough and cold preparations including decongestants, hormones such as estradiol, and other steroids, including corticosteroids, hypnotics, immunosupressives, muscle relaxants, para sympatholytics, psychostimulants, sedatives and tranquilizers.

Pharmaceuticals representative of the classes described hereinabove are described in Goodman and Gilman's, The "The Pharmacological Basis of Therapeutics, 8th edit.

For example, in an embodiment of the present invention, the antihistamine chlorpheniramine maleate is encapsulated in gluten and is processed to a free flowing powder according to the methods described herein and in 2 copending applications U.S. application Ser. No. 08/697,935 entitled "Spray Techniques for Making Novel Compositions Containing Gluten and Polysaccharides that Contain Uronic Acid Residues Useful for Encapsulating Fat, Oils and Solids" and U.S. application Ser. No. 08/706,855 entitled "Double Emulsion Techniques for Making Novel Compositions Containing Gluten and Polysaccharides that Contain Uronic Acid Residues Comprising the Use of Inert Carriers and Precipitating Salt Useful for Encapsulating Fats, Oils and Solids", filed concurrently Sep. 3, 1996. The chlorpheniramine maleate encapsulated in gluten can be blended with other pharmaceutical excipients and carriers known to those skilled in the art, and is suitable for tabletting.

Representative solid agricultural chemicals include, but are not limited to, S-2,3,3-trichlorallyl di-isopropyl (thiocarbamate) (tri-allate) and 3,6-dichloropyridine-2-carboxylic acid (3,6dichloropicolinic acid), esters of (±)-2 [4-(5-trifluoromethyl-2-pyridyloxy)phenoxy]propionic acid (Fluazifop), the butyl ester thereof (Fluazifop butyl) and esters of (±)-2[4-(3-chloro-5-trifluoromethyl-2-pyridyloxy) -phenoxy]propionic acid (Dowco 453) such as the ethoxyethyl ester thereof.

Other suitable herbicides are derivatives of urea, carboxylic acid ester, amino-acids, diphenylethers, phenylcarbamates, s-triazine, as-triazinones, heterocycles, s-triazindiones, phenylpyridaziones, benzofuran, quinoline carboxylic acids, phenoxy acetic acids phenoxy propionic acids, and benzene sulphonamides.

Examples of herbicidally active ureas are:
3-(3-chloro-p-toly)-1,1dimethylurea (Chlortoluron), 3-(4-isopropylphenyl) 1,1dimethylurea
(Isoproturon), 3-(3,4-dichlorophenyl)-I-methoxy-1-methylurea (Linuron),
1-(benzothiazol-2-yl)-1,3-dimethylurea (methabenzthiazuron), and
3-(3-chloro-4-methoxyphenyl)-1,1-dimethylurea) (Metoxuron).

Examples of herbicically active carboxylic acid esters are:
ethyl N-benzoyl-N-(3,4-dichlorphenyl)-DL-alaninate (Benzoylprop-ethyl), isopropyl N-benzoyl-N-(3-chloro-4-fluorophenyl)-DL-alaninate (Flamprop-isopropyl), and methyl N-benzoyl-N-(3-chloro-4-fluorophenyl)-DL-alaninate (Flamprop-methyl), esters of (±)-2-[4-(3-chloro-5-trifluoromethyl-2-pyridyloxy)phenoxy] propionic acid (Dowco 453), esters of (±)-2-[4-(6-chlorobenzothiazol-2-yloxy)-phenoxy]propionic acid (Fenthiaprop), such as the ethyl ester (Fenthiaprop-ethyl) esters of (±)-2-[4-6-chlorobenzoxazol-2-yloxy)phenoxy]

propionic acid (Fenoxaprop), such as the ethyl esters (Fenoxaprop-ethyl), (±)-2-[4-3,5-dichloro-pyridyloxy)phenoxy]propionic acid-2-benzyloxy-esters, methyl 3-[1-(allyloxyimino)butyl]-4-hydroxy-6,6-dimethyl-2-oxocyclohex-3-ene carboxylate (Alloxydim) and lower esters of phenoxy acetic acidand phenoxy propionic acid such as 2, 4-D, MCPA, Dichlorprop and Mecoprop.

Examples of herbicidally active amino acids are:

N-(phosponomethyl)glycine (Glyphosate) as acid or in salt form, and (±)-2-amino-4-(hydroxymethylphosphinyl)butanoic acid (Glufosinate) as acid or in salt form.

Examples of herbicidally active diphenylethers are:

2,4-dichlorophenyl-4-nitrophenyl ether (Nitrofen), and 5-(2-chloro-a,a,a,-trifluoro-p-tolyloxy)-2-nitrobenzoic acid (Acifluorfen).

Examples of herbicidally active phenylcarbamates are:

3-[(methoxycarbonyl)aminophenyl)amino]phenyl-N-(3'-methyl-phenyl)carbamate (Phenmedipham), and ethyl 3-phenylcarbamoyloxyphenylcarbamate (Desmedipham).

Examples of herbicidally active s-triazines are:

2-(4-chloro-6-ethylamino-1,3,5-triazin-2-ylamino)-2-methylpropioni-trile (Cyanazine), 2-chloro-4,6-bis(ethylamino)-1,3,5-triazine (Simazine), 2-tert-butylamino-4-ethylamino-6-methylthio-1,3,5-triazine (Terbutryne), and 2-chloro-4-ethylamino-6-isopropylamino-1,3,5-triazine (Atrazine).

Examples of herbicidally active as-triazin-5-ones are:

4-amino-4,5-dihydro-3-methyl-6-phenyl-1,2,4-triazin-5-one (Metamitron), 6-tert-butyl-4-isobutylideneamino-3-methylthio-1,2,4-triazin-5(4H)-one (Isomethiozin), and 6-tert-butyl-4-isobutylideneamino-3-methylthio-1,2,4-triazin-5(4H)-one (Isomethiozin), and 4-amino-6-tert-butyl-4,5-dihydro-3-methylthio-1,2,4-triazin-5-one (Metribuzin).

An example of herbicidally active heterocyclic componds is:

3-isopropyl-1-(H)-benzo-2,1 3-thiadiazin-4-one-2,2-dioxide (Bentazone).

An example of herbicidally active s-triazindiones is:

3-cyclohexyl-6-dimethylamino-1-methyl-1,3,5-triazine-2,4 (1H,3H)-dione (Hexazione).

An example of herbicidally active sulfonamides is:

1-(2-chlorophenylsulphonyl-3-(4-methoxy-6-methyl-1,3,5-triazine-2-yl)urea (Chlorsulfuron).

An example of herbicidally active phenylpyridazinones is:

5-amino-4-chloro-2-phenyl-3(2H)pyridazinone (Chloridazon).

An example of herbicidally active benzofurans is:

(±)-2-ethoxy-2,3-dihydro-3,3-dimethylbenzofuran-5-yl methanesulphonate (Ethofumesate).

Examples of herbicidally active phenoxy acetic acids and phenoxy propionic acids are:

2,4-dichlorophenoxy acetic acid (2,4-D)

4-chloro-2-methylphenoxy acetic acid (MCPA)

(±)-2-(2,4-dichlorophenoxy)propionic acid (Dichlorprop)

(±)-2-(4-chloro-2-methylphenoxy)propionic (Mecoprop) and (±)-2-[4-(4-chlorophenoxy)phenoxy]propionic acid.

In compositions comprising the above-mentioned active acids, at least part of the acids may be present in salted form.

An example of herbicidally active active quinoline carboxylic acids is:

7-chloro-3-methyl-quinoline-8-carboxylic acid (BASF 518H).

The wide variety of agricultural chemicals useful in the practice of the present invention are described in "The Herbicide Handbook", published by Weed Science Society of America, 7th edition, incorporated by reference herein.

Preferably, solids are used at levels of 0.01 to 85%, more preferably 0.01 to 70%, most preferably 0.01 to 40%.

Gluten Useful in the Practice of the Present Invention

Gluten useful in the practice of the present invention includes wheat and corn gluten. Both wheat and corn gluten are suitable for encapsulating fats, oils, and solids. Wheat gluten is preferred because of its low cost. However, corn gluten is particularly suited for use in preparing edible compositions for those allergic to wheat gluten, e.g Celiac sprue patients. Preferably, gluten is used at levels of 14.5 to 97%, more preferably 30 to 60%, most preferably 40 to 70%.

Polysaccharides that Contain Uronic Acid Residues Useful in Solubilizing Gluten Polysaccharides that contain uronic acid residues useful in solubilizing gluten are described in U.S. Pat. No. 5,738,805 entitled "Process for Solubilizing Gluten That Normally Is Capable of Absorbing Water Without Dissolution ", which describes a method of solubilizing gluten using polysaccharides that contain uronic acid residues. Said patent is incorporated by reference herein.

Specifically, useful polysaccharides that contain uronic acid residues include, but are not limited to, both high and low methoxyl pectins, algin (e.g sodium alginate) or its salts, gum arabic, gum tragacanth, gum karaya, gum ghatti, xanthan gum, gellan gum, and seed mucilages.

Said polysaccharides that contain uronic acid residues are used at a level of at least 3% of the level of gluten, preferably at a level of 3 to 150% of the level of gluten, more preferably at a level of 3 to 75% of the level of gluten, and most preferably at a level of 3 to 20% of the level of gluten.

Optional Ingredients Useful in the Compositions of the Present Invention

Optional ingredients useful in the present invention include, but are not limited to, resins, fillers, binders, lubricants, solvents, glidants, disintegrants, co solvents, surfactants preservatives, sweetening agents, flavoring agents, buffer systems, pharmaceutical grade dyes or pigments and viscosity agents.

Flavoring agents useful herein include, but are not limited to, those described in Remington's Pharmaceutical Sciences, 18th Edition, Mack Publishing, 1990, pp1288–1300 and Furia and Pellanca, Fenaroli's Handbook of Flavor Ingredients, The Chemical Rubber Company, Cleveland, Ohio, 1971. A compilation of suitable flavorings can also be found in the Code of Federal Regulations, at 21 CFR Parts 170–197.

Dyes or Pigments useful in the present invention include those described in the Handbook of Pharmaceutical Excipients, pp81–90, 1986 by the American Pharmaceutical Association and the Pharmaceutical Society of Great Britain.

Preferred cosolvents include, but are not limited to, ethanol, glycerin, propylene glycol, polyethylene glycols.

Preferred buffer systems include, but are not limited to, acetic, boric, tartaric, carbonic, succinic, maleic, citric, acetic, benzoic, phosphoric, lactic, glyceric, glutaric, and glutamic acids and their sodium, potassium and ammonium salts.

Preferred surfactants include, but are not limited to, polyoxyethylene sorbitan fatty acid esters, polyoxyethylene monoalkyl ethers, sucrose monoesters, lanolin esters, alkyl sulfate salts.

Preferred preservatives include, but are not limited to, phenol, alkyl esters of parahydroxybenzoic acid, citric acid, o-phenylphenol benzoic acid, boric acid, sorbic acid, chlorobutanol, benzyl alcohol, thimerasol, phenylmercuric acetate, benzalkonium chloride, cetylpyridinium chloride, and methyl paraben and propyl paraben.

Preferred sweeteners include, but are not limited to, sucrose, glucose, saccharin, sorbitol, mannitol, aspartame.

Preferred viscosity agents include, but are not limited to, the water soluble celluloses such as methyl cellulose, sodium carboxymethylcellulose, hydroxypropyl cellulose, hydroxymethyl cellulose, and ethyl cellulose and hydroxyethyl cellulose.

Preferred fillers include, but are not limited to, lactose, mannitol, sorbitol, tribasic calcium phosphate, compressible sugar, starch, calcium sulfate, dextro and microcrystalline cellulose.

Preferred lubricants include, but are not limited to, magnesium stearate, stearic acid, and talc. Preferred glidants include, but are not limited to, talc and colloidal silicon dioxide. Preferred disintegrants include, but are not limited to, starch, sodium starch glycolate, crospovidone, croscarmelose sodium, and microcrystalline celullose.

Preferred binders include, but are not limited to, hydroxypropyl cellulose, pregelatinized starch, gelatin, povidone, hydroxypropylmethyl cellulose, methylcellulose, sucrose, sorbitol, and ethylcellulose.

Optional ingredients are used at a level of 0 to 95%. Preservatives and antioxidants are useful in the compositions of the present invention at levels of 0–5%.

Making the Composition of Present Invention

The gluten is solubilized according to the methods described in U.S. Pat. No. 5,738,805 entitled "Process for Solubilizing Gluten That Normally Is Capable of absorbing Water Without Dissolution", and incorporated by reference herein. The gluten solubilized with a polysaccharide that contains uronic acid residues is prepared as described in the said CIP application. The solid or liquid is then added to prepare the compositions of the present invention according to the methods described hereinbelow. Further, methods for making the composition of the present invention are the subjects of 2 co-pending applications entitled "Spray Techniques for Making Novel Compositions Containing Gluten and Polysaccharides that Contain Uronic Acid Residues Useful for Encapsulating Oils ands Solids" and "Double Emulsion Techniques for Making Novel Compositions Containing Gluten and Polysaccharides that Contain Uronic Acid Residues Useful for Encapsulating Oils ands Solids", U.S. patent application Ser. Nos. 08/697,935 and 08/706,855 respectively filed concurrently with the present application on Sep. 3, 1996. Examples 1–9 are specific, but not limiting, examples illustrative of how to prepare the compositions of the present invention.

General Methods of Encapsulation

Spray Drying

Spray drying is a common method of encapsulating oils or solids and is well known to those skilled in the art. This type of encapsulation is done for a variety of reasons, to make liquids into powders, protect encapsulants from degradation, and to slow the release of the encapsulants. Typically, a solution is prepared by dissolving the binder which is typically a hydrocolloid such as gelatin, water-soluble starch, or a water-soluble cellulose and other ingredients such as fillers, surfactants, etc, then the oil or solid is added and emulsified in the case of an oil or dispersed in the case of a solid into the solution of the binder. The emulsion or dispersion is then pumped to a spray drying chamber and atomized into small droplets by one of several methods. The atomized droplets contact hot air (usually above 150° C.) that is conveyed into the drying chamber by blowers and the water is evaporated, leaving a powder which consists of fine oil droplets in a matrix of dry encapsulating agent. This particular method usually produces relatively small particles compared to other methods.

However, it is sometimes desirable to make a larger particle since the oil or solid is better stabilized against the chemical and temperature extremes of many manufacturing processes or end-use environments. Additionally, since the spray-drying processes are very rapid, the powder particles tend to be porous due to the rapid evaporation of the water. Further, when higher temperatures are used this method may not be suitable for heat sensitive ingredients. Also, the protective binders do not get much time to align and bond to each other to form as strong protective matrix as is possible. A spray drying process has an upper limit to the particle size that can be produced. As the particles become larger, the droplet dries more slowly owing to the reduction in particle surface area per unit volume from which the evaporation needed to dry the particle takes place. If the particles are too large they will impact the walls of the dryer while still wet and will stick, leading to tower build up and poor yields. To further increase the particle size, and provide more stability when needed, or to avoid thermal degradation during drying, an alternate method must be used to produce the particle.

Spray Congealing

If the encapsulating binder is capable of gelling, spray cooling, also known as spray congealing, can be employed. It is well known in the art that gelatin emulsions can be sprayed into a fluidized cloud or bed of starch or into a cloud of hydrophobic silica or other coating agent such that the resultant starch or silica coating prevents the liquid particles from sticking to each other. Subsequent to the particle formation, they are dried utilizing methods known to those skilled in the art, including but not limited to, fluid bed drying, rotary vacuum drying, ribbon blender drying, flash drying and mechanical fluidized bed drying, with what is typically ambient or at least lower temperature air than the spray drying process. A gelling binder such as gelatin is needed so that the liquid droplets, after they are coated, gel and gain some mechanical strength so that they remain intact as they are dried according to methods known to those skilled in the art, including but not limited to, fluid bed drying, rotary vacuum drying, ribbon blender drying, flash drying or mechanical fluidized bed drying. As an alternative to to a gelling hydrocolloid, it is possible to add appropriate ingredients that will over time react to provide a gel such as calcium salts with pectins and alginates. Since the drying is much slower, generally hours at a time, the beadlets which are generally much larger than those made via traditional spray drying are less porous than spray-dried powders. And, the slow drying allows some of the binders to hydrogen bond to each other to form a tighter protective matrix then that achievable with traditional spray drying. In the case of starch coated beadlets, the starch coating itself can provide an additional protective barrier.

Modified Spray Drying

As stated above, to be able to spray congeal, the binders need to be able to gel to provide mechanical strength to survive the early stages of fluid-bed drying. For those cases where the larger and less porous beadlets are needed but the binders are incapable of gelling, modified spray drying can be incorporated.

Modified Spray drying of oils or solids is also known to those skilled in the art and has been well described, in U.S. Pat. No. 5,460,823, U.S. Pat. No. 4,990,280, and U.S. Pat. No. 4,870,196, incorporated by reference herein. In the modified spray drying process the suspension or emulsion is preferably sprayed at a temperature of from 5° to 99° C. and at a viscosity of from 50 to 300 mPa using an atomizing nozzle or an atomizing wheel in a spraying chamber, wherein the temperature is from 50° to 95° C. A powdery spraying excipient may be blown into the spraying chamber in order to prevent agglomeration of the formed microcapsules and to prevent adherence to the chamber wall. The spraying excipient is preferably supplied in an amount of from 5 to 50 percent by weight based on the weight of the final product. The powdered microcapsules may be transferred to a fluidized bed, wherein they may be transferred to a fluidized bed, wherein they may be dried to a residual water content of between 0 to 10% (preferably from 2 to 5%) and excessive spraying excipient is separated. The drying air temperature is preferably from about 0° to about 60° C.

Spray Formulation

Another variation of modified spray drying and spray congealing is the use of a hydrophic silica to coat the outside of the newly formed wet beadlets instead of starch. This process is generally referred to as spray formulation. See U.S. Pat. No. 4,519,961, incorporated by reference herein.

Double Emulsion Technique

An older technique, that is sometimes performed particularly in laboratories where the availability of suitable spraying systems is limited, is the double emulsion technique. In this process, a primary emulsion is prepared as already described. This emulsion is then dispersed in hot mineral oil. Thus a oil-in-water-in-oil emulsion (double emulsion) is formed. This mix is cooled until the primary (aqueous) emulsion has congealed and typically a powdery coating agent is added to prevent sticking of the beadlets. After coating, the beadlets are filtered and washed with a low boiling petroleum solvent to remove the residual mineral oil. These washed beadlets are then air dried.

In the spray drying, modified spray drying, spray congealing, spray formulation, and double emulsion processes the following spraying excipients may be used: starches, modified starches, tricalcium phosphate, lactose, mannitol, ethyl cellulose, coagulated albumin, hardened gelatin, casein, calcium stearate, sodium stearate, metal soaps, hydrogenated recinus (castor) oil, polyoxide, talcum, waxes and silicates." Additionally, gluten can be used to encapsulate oils and solids in gluten. It is known to those skilled in the art, that gluten can be solubilized in acid or base, and this solubilized the gluten can be used to form a stable emulsion. And said emulsion can be spray dried.

In the above processes the binders typically provide adequate protection to the encapsulants as long as they are powders and not exposed to high moisture or wet conditions, particularly in the presence of mechanical stress. In such cases the protective binders will soften or dissolve if enough water is present. If so, the powders or beadlets can fall apart. If they are exposed to pelleting or extrusion processes that are commonly employed in feed, food, and some other agricultural applications, high moisture, steam, and severe mechanical stress are employed. In such cases the protective powders are substantially destroyed, and sensitive encapsulants can be destroyed or layed open to quick degradation on storage. It is already known in the art that gelatin-based beadlets made can be made substantially water-insoluble by chemical and thermal crosslinking. This requires additional processing and can be somewhat deterimental to the encapsulants during this processing.

General Discussion of Methods of Encapsulating Oils and Solids of the Present Invention While knowledge of these encapsulating processes, including the addition of optional ingredients as disclosed herein, exists, it is not taught that the compositions containing gluten and polysaccharide containing uronic acid residues, useful for encapsulating oils and solids, can be prepared by these encapsulating processes. Further, it is not taught in the art that the gluten solubilized with polysaccharides that contain uronic acid residues which is prepared by these various processes will remain insoluble, and thus, an optimal encapsulating agent.

The following specific, non-limiting examples illustrate the techniques useful for encapsulating fats, oils and solids with gluten and polysaccharides containing uronic acid residues.

EXAMPLE 1

Spray Drying Vitamin D Oil 13,217 grams of water are heated with a hot plate in a 5-gallon tank to about 50° C. A homogenizer is used to dissolve 584 grams of Pectin HM slow set. The temperature in the tank is maintained at about 40° to 60° C. throughout the preparation of the emulsion. 1,941 grams of vital wheat gluten are dissolved using the homogenizer, forming an aqueous solution of pectin and gluten in water. Ethoxyquin (112 grams) and vitamin D oil of 10 million International Units (i.u.) potency (136 grams) are homogenized into the aqueous solution, forming an emulsion. A total of 0.4 grams of Dow Corning type FG antifoam, are added to control foaming. A Niro Utility spray dryer is used to dry the emulsion. The inlet air temperature is about 200° C. The emulsion was transferred to a stirred tank and a gear pump was used to feed the emulsion. The emulsion is atomized by a 5-inch slotted wheel rotating at 19,000 rpm. Silica is fed from a loss-in-weight screw feeder at about 0.7% of the liquid feed rate. Outlet temperature is approximately 132° C. and feed rate varies between 100 and 130 grams/minute. The powder is collected in a cyclone.

The powder is fine and free flowing with 74% of the particles being between 325 and 100 mesh. The powder tapped bulk density is 0.36 gm/cc and moisture 3.4%. Flowability is high—material freely flows through a 5-mm hole in a disc. The assay, at 519,000 i.u./gram meets the targeted assay, indicating that none of the vitamin D degraded. A 2-gram sample of this powder is placed in 100 ml of boiling water and is held there for 5 minutes. After removal from the heat, a large quantity of sediment settles rapidly to the bottom of the flask, indicating the powder is insoluble.

The powder from Example 1 is pelleted into poultry boiler feed. The feed formula is shown below:

| INGREDIENT | WEIGHT, LBS. |
| --- | --- |
| Corn Meal | 3382 |
| Soy Bean Meal | 642 |
| Wheat Midds | 364 |
| Soy Bean Oil | 96 |
| Dicalcium Phosphate 22–18.5 | 82 |
| Fish Meal | 52 |
| Limestone | 48 |
| IOFIXT ™ (salt w/minerals) | 48 |
| Trace Minerals* | 28 |
| Meat Meal | 28 |
| Bone Meal | 20 |
| Mold Inhibitor | 10 |
| TOTAL | 4800 |

| TRACE MINERALS | AMOUNT (ppm) |
| --- | --- |
| Cobalt | 3 |
| Copper | 60 |
| Iron | 250 |
| Manganese | 170 |
| Selenium | 0.2 |
| Zinc | 350 |
| Iodine | 5 |

The feed is blended in a Sprout-Bauer B-11 ribbon blender. The vitamins are pre-blended in a plastic bag with 1 to 2 kilogram feed, and then added to 400 lbs. of feed in the blender. The vitamin D powder from Example 1 is charged to give an ending feed assay of 1,000,000 i.u./kilogram. The material is then mixed for 2.5 minutes in each direction. The pellet mill (Sprout-Bauer 501-D pellet mill, with feeder/conditioner and steam) is conditioned with blank meal. The meal is then pelleted using a $^{13}/_{64}$"×1¾" die, with steam conditioning at 200° F. The pellets are allowed to cool and the final moisture is between 10 and 12%. The samples are assayed initially and placed in an environmental chamber maintained at 40° C. and 70% relative humidity. The pellets are sampled and assayed every two weeks. Over a period of 12 weeks, the drop in potency is no more than 7%, indicating good stability.

EXAMPLE 2

Spray Drying, Vitamin A Acetate

The methods of Example 1 are used to make a gluten/vitamin A acetate aqueous emulsion, eliminating the ethoxyquin (its in the oil) and substituting vitamin A acetate for vitamin D oil. Charges include: 5856 grams of water, 339 grams of Pectin HM slow set, 1125 grams of vital wheat gluten, and 680 grams of vitamin A acetate oil (1.8 million i.u./gram). No antifoam is needed. The inlet air is at 200° to 205° C., the outlet air at 127° to 130° C., and the feedrate at 110 grams/min. The wheel is again at 19,000 rpm and 0.7% of the liquid feed rate of Sipernat D17 hydrophobic silica is fed to the drying chamber.

The powder produced is moderately free flowing, had a 586,000 i.u./gram vitamin A acetate assay versus an expected 585,000 i.u. expected. About 88% of the particles are between 100 and 200 mesh. LOD was 1.7% with bulk density of 0.28 gm/cc. Using the same boiling test, the sample is found to be insoluble.

EXAMPLE 3

Spray Drying Encapsulation of Solids—Riboflavin in Gluten/Pectin 3664 grams of water are heated with a hot plate in a 2-gallon tank to about 50° C. A homogenizer is used to dissolve 73 grams of Pectin HM slow set. The temperature in the tank is maintained at about 40° to 50° C. throughout the preparation of the slurry. 583 grams of vital wheat gluten aree dissolved using the homogenizer, forming an aqueous solution of pectin and gluten in water. 680 grams of riboflavin, a dusty, clinging, static-prone powder, is slowly homogenized into the solution, forming a slurry. A Niro Utility spray dryer is used to dry the slurry. The inlet air temperature is about 190° C. The slurry is transferred to a stirred tank and a gear pump is used to feed it into the dryer. The slurry is atomized by a 5-inch slotted wheel rotating at about 19,000 rpm. Silica is fed from a loss-in-weight screw feeder at about 0.7% of the liquid feed rate. The feed rate is adjusted to yield an outlet temperature of approximately 110° C. The powder is collected in a cyclone. The powder is found to have a moisture content of less than 5% and to be free flowing. Using the same boiling test, the sample is found to be insoluble.

EXAMPLE 4

Modified Spray Drying, Vitamin A Acetate

An emulsion is prepared as in Example 3 using 938 grams of 1.8 million i.u./gm vitamin A acetate oil, 328 grams of Pectin HM slow set, 1088 grams of vital wheat gluten, 5646 grams of original water per the method of Example 3. Additional water of 4250 grams is added to adjust the viscosity to about 350 cp.

The emulsion is fed at about 50 grams/min and atomized in the drying chamber. Dryflo® (hydrophobic) starch is fed at the rate of 200% of the liquid feed, and hot air at 95° to 98° C. is introduced into the tower to aid in forming the starch cloud and drying the beadlets. The beadlets with the excess starch are transferred to a 100-mm glass fluidized bed. Air at 43° to 51° is fed and the material is fluidized. The excess starch is blown off and the beadlets dried.

The resulting beadlets are free flowing with a much coarser size distribution than the spray dried powders. 85% of the beadlets are between 20 and 60 mesh. Loss on drying was 2.4% and tapped bulk density is 61. The powder freely flows through a 6 mm diameter hole. It is also found by the method of Example 1 that the beadlets remain intact for 1.5 minutes in boiling water. After this time, some breakup of the beadlets can be seen, but still, a large amount of sediment can be observed. No free oil is observed on the surface of the water after settling. This indicates that a substantial amount of integrity is present in the beadlets, and that the gluten itself is rendered substantially insoluble in boiling water by the process. These facts indicate that the oil was still for the most part encapsulated, which would impart protection in both pelleting and extrusion applications. When an oil is not properly encapsulated in such a test, free oil is observed on the liquid surface after settling has taken place.

EXAMPLE 5

Preparing a Vitamin Powder Via Double Emulsion Process with Gelatin 200 grams of water are heated with a hot plate in a 600-ml beaker to about 50° C. as 25 grams of a gelling agent, such as gelatin (Sanofi Type A, Pork Skin), is added. Once the gelatin is dissolved, the beaker is removed from the heat and cooled to about room temperature. To the gelatin solution three grams of algin (Kelco Kelgin xl/f) is added while agitating. Next, 40 grams of gluten are mixed in with a high shear mixer. An additional 50 grams of water are added to reduce viscosity. The primary emulsion is formed by adding 680 grams of vitamin A acetate oil (1.8 million i.u./gram) to this mixture and is homogenized with the high shear mixer as the temperature rises from 45° C. to 60° C. The secondary emulsion is formed by adding the primary emulsion to 400 grams of light mineral maintained at 60° C. in a round-bottom flask. This mixture is agitated enough so that the aqueous emulsion droplets are about 100 microns in size in the mineral oil. The flask is then placed in an ice-water bath. When the temperature of the mixture reaches about 20° C. the agitation is slowed to that enough to maintain a suspension. When the mixture reaches 6° C., 26 grams of a powdery coating agent such as Dryflo® (hydrophobic) corn starch is added. After about five minutes, the mixture was diluted with about an equal volume of petroleum ether (boiling point 60°–90° C.). This mixture is poured into a fritted-glass filter which was connected to a filter flask under reduced pressure. The filtered beadlets are washed with three more volumes of petroleum ether. After completely draining, the beadlets are dried by blowing a gentle stream of nitrogen through the bottom of the filter. The next day the lose clumps of beadlets are broken up on 20-mesh screen. The beadlets are subjected to the boiling test as desribed above and the beadlets are substantially insoluble.

EXAMPLE 6

Preparing a Vitamin Powder Via Double Emulsion Process with a Precipitating Salt To 200 grams of water three grams of algin (Kelco Kelgin xl/f) are added while agitating. Next, 40 grams of gluten are mixed in with a high shear mixer. The primary emulsion is formed by adding 680 grams of vitamin A acetate oil (1.8 million i.u./gram) to this mixture and is homogenized with the high shear mixer as the temperature rises from 45° C. to 60° C. Next 1 gram of a gelling salt such as dicalcium phosphate is added and mixed for one minute. The secondary emulsion is formed by adding the primary emulsion to 400 grams of light mineral maintained at 60° C. in a round-bottom flask. This mixture is agitated enough so that the aqueous emulsion droplets are about 100 microns in size in the mineral oil. The mixture is kept at 60° C. for 20 minutes after which the agitation is slowed enough to maintain a suspension. The flask is then placed an ice-water bath. When the temperature of the mixture reaches about 20° C., 26 grams of a powdery coating agent such as Dryflo® (hydrophobic) corn starch are added. After about five minutes, the mixture is diluted with about an equal volume of petroleum ether (boiling point 60°–90° C.). This mixture is poured into a fritted-glass filter which is connected to a filter flask under reduced pressure. The filtered beadlets are washed with three more volumes of petroleum ether. After completely draining, the beadlets are dried by blowing a gentle stream of nitrogen through the bottom of the filter. The next day the lose clumps of beadlets are broken up on 20-mesh screen. The beadlets are subjected to the boiling test as desribed above and the beadlets are substantially insoluble.

EXAMPLE 7

Preparing a Vitamin Powder Via Spray Congealing with Gelatin 200 grams of water are heated with a hot plate in a 600-ml beaker to about 50° C. as 25 grams of gelatin (Sanofi Type A, Pork Skin) is added. Once the gelatin dissolves, the beaker is removed from the heat and cooled to about room temperature. To the gelatin solution three grams of algin (Kelco Kelgin xl/f) are added while agitating. Next, 40 grams of gluten are mixed in with a high shear mixer. An additional 50 grams of water are added to reduce viscosity. 680 grams of vitamin A acetate oil (1.8 million i.u./gram) is then added to this mixture and homogenized in with the high shear mixer as the temperature rises from 45° C. to 60° C. This emulsion is sprayed into a small tower fitted with a fluidized bed into which a cocurrent stream of Dryflo corn starch is added. Upon completion of the spraying the fluidization of the bed is continued until the powdered beadlets are substantially dry. The powdered beadlets are sieved through a set of 20 mesh and 200 mesh screens to remove coarse agglomerates and starch that did not coat the beadlets. The beadlets are subjected to the boiling test as desribed above and the beadlets are substantially insoluble.

EXAMPLE 8

Gluten Encapsulated Oils in a Blender of Inert Carrier and Precipitating Salt An emulsion is prepared as in Example 4, using 2497 grams of vitamin A acetate (2.1 million iu/gm oil), 2784 grams of vital wheat gluten, 126 grams of pectin LM-35, 742 grams of ISOSWEET 5500 (fructose/glucose/ corn syrup blend), and 11,249 grams of water. 116 kg of Dryflo® modified corn starch are mixed with 1.16 kg of calcium acetate in a nominal 30-gallon ribbon blender. A paint sprayer (Wagner painter) is used to spray the emulsion into the top of the blender while agitating the starch/calcium mixture. The sample is sufficiently solidified to determine particle size without drying. A sample is taken from the blender and sifted with the following results:

| BLENDER PRODUCED GLUTEN ENCAPSULATED OIL PARTICLE SIZE | |
|---|---|
| MESH | % THRU |
| 20 | 100.0 |
| 40 | 99.7 |
| 60 | 97.0 |
| 80 | 91.1 |
| 100 | 88.5 |
| 120 | 75.6 |
| 200 | 59.7 |
| 325 | 7.2 |

EXAMPLE 9

Gluten/Pectin Encapsulation of Vitamin A by Spray Formulation

An emulsion is prepared per the method of Example 1 using 938 grams of feed grade vitamin A acetate oil (but with 2.1 million i.u./gm), 328 grams of Pectin HM slow set, 1088 grams of vital wheat gluten, 5646 grams of original water. Additional water of about 4000 grams is added to adjust the viscosity to about 350 cp for spray.

The emulsion is fed at about 100 gm/min and atomized in the spray chamber. Sipernat®D-17 hydrophobic silica (Degussa Corp.) is fed at a rate of about 5% of the liquid feed with sufficient air flow to convey the silica into the tower and form a silica cloud, and the material is collected in a container at the bottom of the tower. The wet silica coated beadlets and the excess silica are transferred to a fluid bed and dried by gently fluidizing first with ambient air, then as the beadlets increase their mechanical strength by drying off the water, the fluidizing air is heated to about 60° C. and the flow rate increased to blow off the excess silica. The resulting dry beadlets retain about 4% hydrophobic silica as a coating on their surface, and are freeflowing. The formula is suitable for pelleting and extrusion of animal feed.

Utility of the Present Invention

Fats, oils, and solid ingredients encapsulated in gluten solubilized in polysaccharides that contain uronic acid residues can be used to formulate sprayable agricultural formulations, powdered vitamin and pharmaceutical products. Further, unpleasant tasting ingredients such as pharmaceuticals can be encapsulated for taste-masking purposes. Also, said fats, oils, and solids encapsulated in gluten solubilized in polysaccharides containing uronic acid residues can be subject to the harsh conditions of extrusion and pelleting techniques known to those skilled in the art. Moreover, fats, oils, and solid ingredients encapsulated in gluten solubilized in polysaccharides that contain uronic acid residues are useful for preparing time-release formulations for pharmaceutical and agricultural applications. Finally, the compositions need not be spray dried and can be used to formulate liquid formulations of fats, oils ans solids. The following non-limiting examples illustrate the utility of the present invention

Utility Example 1

A powdered pharmaceutical composition comprising solid pseudoephedrine encapsulated in gluten and polysaccharides containing uronic acid residues is prepared according to methods described herein Said composition can be blended with the optional ingredients described herein, and tabletted according to methods known to those skilled in the pharmaceutical arts

Utility Example 2

A powdered herbicidal composition comprising acifluorfen encapsulated in gluten and polysaccharides containing uronic acid residues is prepared by methods described herein. Said composition is dusted on post emergent crops. By adjusting the various ingredients in the composition, appropriate time-release properties can be obtained.

Utility Example 3

A vitamin encapsulated in gluten and polysaccharides containing uronic acid residues can be blended with optional ingredients as described herein, and tabletted. Also, it can be left in powdered form and is useful as a dietary supplement. The encapsulation provides enhanced stability and taste-making properties for the vitamin.

One skilled in the art understands that the composition of the present invention can be blended with any of the active and inert ingredients described herein and subsequently subjected to extrusion and pelleting processes known to those skilled in the art to produce products in forms acceptable for specific uses., e.g tablets or pellets.

We claim:

1. A composition useful for encapsulating fats, oils and solids comprising:

(a) 14.5 to 97% gluten;

(b) a polysaccharide that contains uronic acid residues, wherein said polysaccharide that contains uronic acid residues is at least 3% of the level of the gluten;

(c) 0.0 to 95% water.

2. A composition according to claim 1, wherein:

(a) said gluten is high or low methoxy pectins or sodium alginate.

3. A composition according to claim 2, wherein:

(a) said wheat gluten is at a level of 30–60%

(b) said high methoxy or low methoxy pectin or sodium alginate is 3–150% of the level of gluten.

4. A composition according to claim 2, wherein:

(a) said wheat gluten is at a level of 40–70%

(b) said high methoxy or low methoxy pectin or sodium alginate is 3–75% of the level of gluten.

5. A composition according to claim 2, wherein:

(a) said wheat gluten is at a level of 40–70%

(b) said high methoxy or low methoxy pectin or sodium alginate is 3–20% of the level of gluten.

6. A composition according to claim 1, which can be pelleted or extruded.

7. A method for encapsulating fats, oils and solids, comprising spray drying said fats, oils, and solids with a composition comprising:

(a) 14.5 to 97%;

(b) a polysaccharide that contains uronic acid residues, wherein said polysaccharide that contains uronic acid residues is at least 3% of the level of the gluten;

(c) 0.0 to 95% water.

8. A method for encapsulating fats, oils and solids, comprising spray congealing said fats, oils, and solids with a composition comprising (a) 14.5 to 97%;

(b) a polysaccharide that contains uronic acid residues, wherein said polysaccharide that contains uronic acid residues is at least 3% of the level of the gluten;

(c) 0.0 to 95% water.

9. A method for encapsulating fats, oils and solids, comprising modified spray drying said fats, oils, and solids with a composition comprising:

(a) 14.5 to 97%;

(b) a polysaccharide that contains uronic acid residues, wherein said polysaccharide that contains uronic acid residues is at least 3% of the level of the gluten;

(c) 0.0 to 95% water.

10. A method for encapsulating fats, oils and solids, comprising spray formulating said fats, oils, and solids with a composition comprising:

(a) 14.5 to 97%;

(b) a polysaccharide that contains uronic acid residues, wherein said polysaccharide that contains uronic acid residues is at least 3% of the level of the gluten;

(c) 0.0 to 95% water.

11. A method for encapsulating fats, oils and solids comprising using inert carrier and precipitating salt techniques to encapsulate said fats, oils, and solids with a composition comprising:

(a) 14.5 to 97%;

(b) a polysaccharide that contains uronic acid residues, wherein said polysaccharide that contains uronic acid residues is at least 3% of the level of the gluten;

(c) 0.0 to 95% water.

12. A method for encapsulating fats, oils and solids comprising using double emulsion techniques to encapsulate said fats, oils, and solids with a composition comprising:

(a) 14.5 to 97%;

(b) a polysaccharide that contains uronic acid residues, wherein said polysaccharide that contains uronic acid residues is at least 3% of the level of the gluten;

(c) 0.0 to 95% water.

* * * * *